United States Patent [19]

Wölfel et al.

[11] 4,364,122
[45] Dec. 14, 1982

[54] X-RAY DIFFRACTION METHOD AND APPARATUS

[76] Inventors: Erich R. Wölfel, Mozartweg 1b, D-6100 Darmstadt; Hans-Georg Diercks, Willersweg 34d, D-2000 Hamburg 62, both of Fed. Rep. of Germany

[21] Appl. No.: 178,442

[22] Filed: Aug. 15, 1980

[30] Foreign Application Priority Data

Aug. 16, 1979 [DE] Fed. Rep. of Germany ....... 2933047

[51] Int. Cl.$^3$ ............................................ G01N 23/20
[52] U.S. Cl. ..................................................... 378/73
[58] Field of Search ........... 250/272, 273, 274, 277 R, 250/277 CH, 278, 279, 280

[56] References Cited

U.S. PATENT DOCUMENTS 3,105,901 10/1963 Ladell .......................... 250/277 CH
3,855,470 12/1974 Sahous ............................. 250/276

*Primary Examiner*—Craig E. Church
*Attorney, Agent, or Firm*—Fred Philpitt

[57] ABSTRACT

X-ray diffraction method and apparatus, especially for studying polycrystalline and liquid substances, are disclosed which employ monochromator focussing on a goniometer circle along whose periphery detector means are movable at twice the angular speed with which a specimen is rotatable in the goniometer center, around the same axis. The specimen is always in the monochromatic convergent beam. The goniometer circle is arranged such that its periphery intersects the longitudinal monochromator center where a pivot may be provided. By selecting the distance between the X-ray source (line focus) and the monochromator center to equal the circle diameter, symmetric focussing is possible. Precision diaphragm means serve to narrow the convergent beams for combined transmission and back-reflection scans that may be quickly effected for intensity and profile evaluation. Special sample holders permit fast exchange of preadjusted specimens and rotation of flat samples parallel to their surface plane for ascertaining preferred orientations (if any).

24 Claims, 11 Drawing Figures

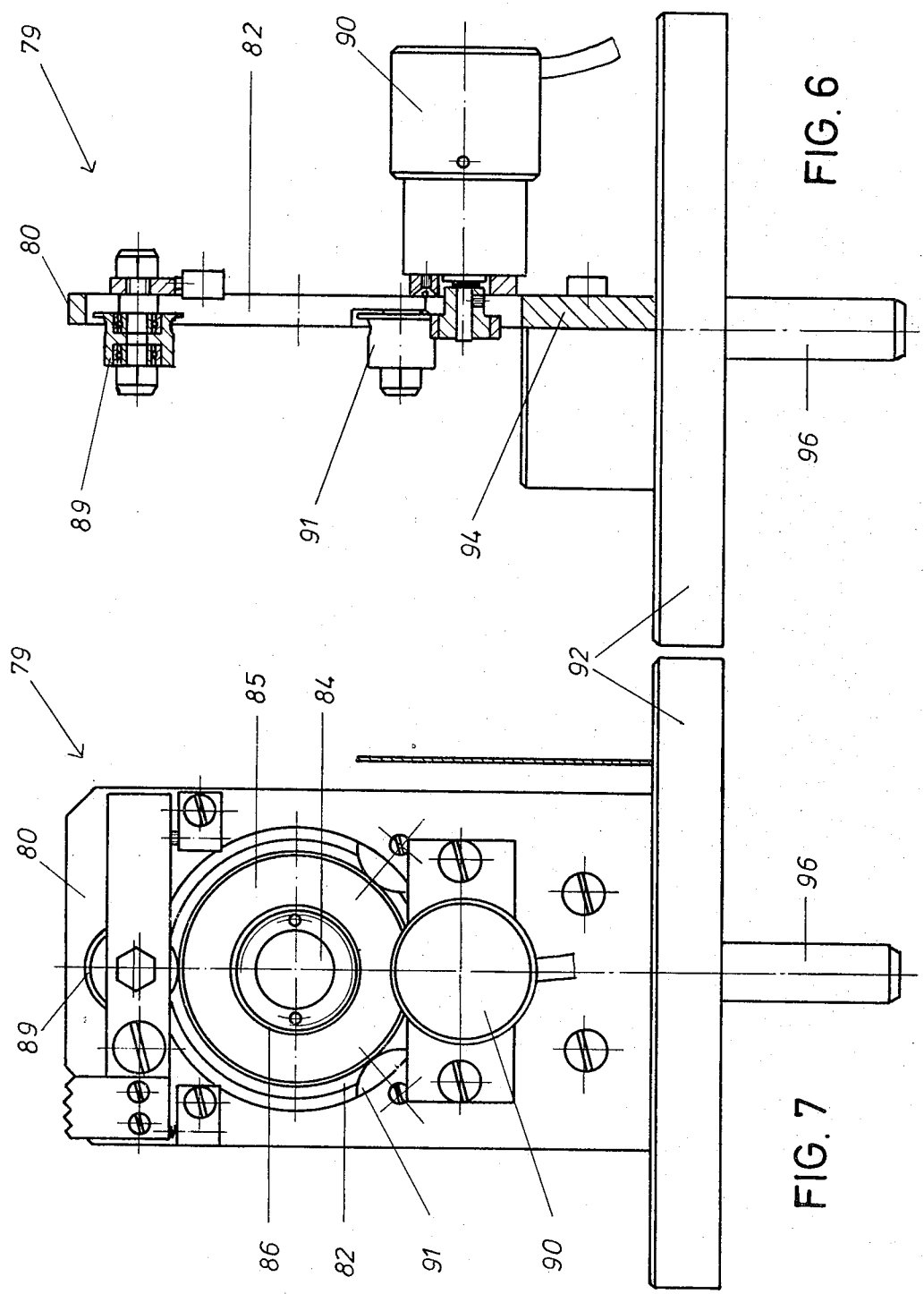

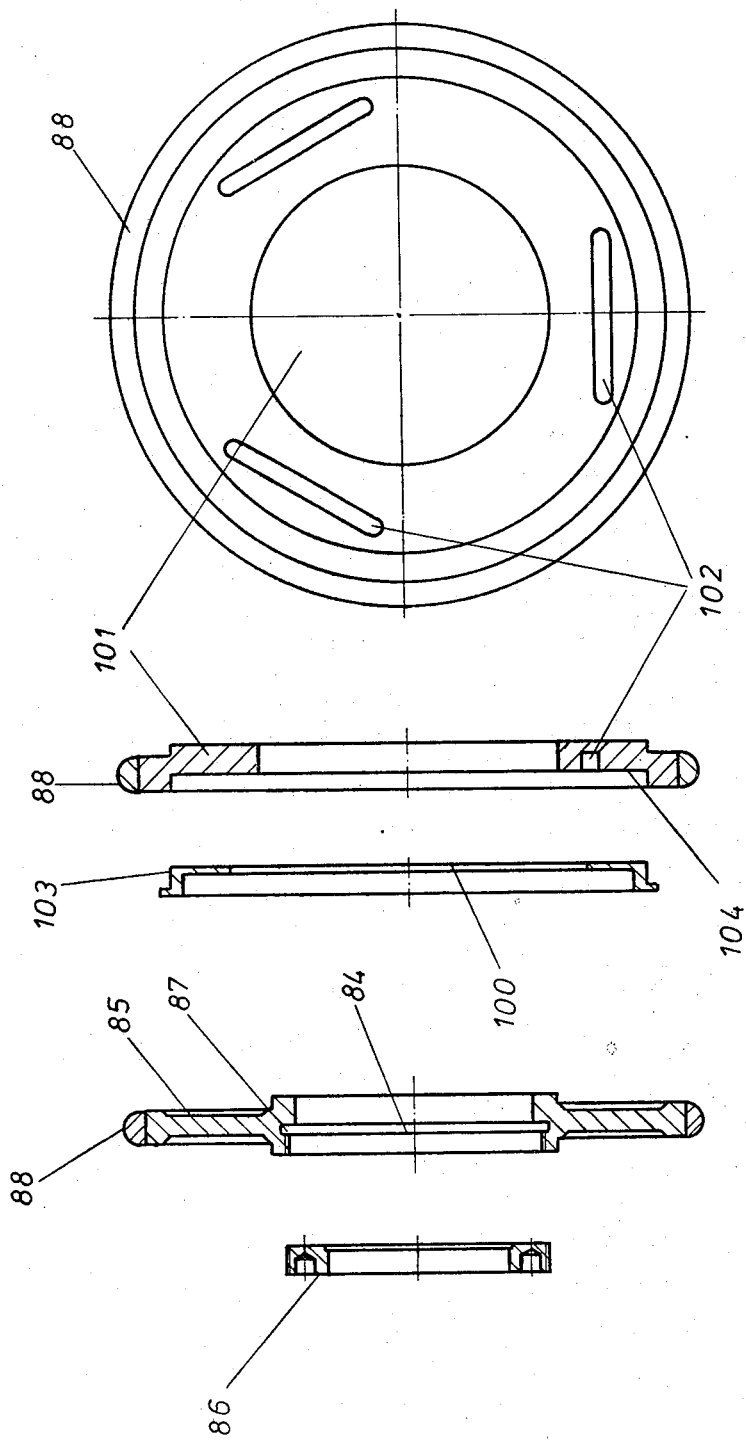

X-RAY DIFFRACTION METHOD AND APPARATUS

BACKGROUND OF THE INVENTION

The present invention relates to improvements in X-ray diffractometry. The known methods and apparatuses for struture analysis of crystalline and liquid substances by means of X-rays are based on the considerations and insights of Laue and Bragg; a qualified survey is offered in the book by H. P. Klug and L. E. Alexander, "X-Ray Diffraction Procedures", New York, 2nd edition, 1974.

For investigating single crystals, an X-ray goniometer as described in DE-PS No. 20 41 031 is advantageous in that it is possible to obtain from the adjusted crystal diffraction patterns according to both the de Jong - Bouman method and the Buerger precession method, which was a remarkable advance over the prior art which required two different apparatuses.

In order to study polycrystalline substances, it is customary to employ diffractometers based on a fundamental method of Debye-Scherrer. Using monochromators, detailed structural analyses become feasible with modern automatic diffractometers working on the Bragg - Brentano principle. In special cases, the modified methods of Seemann - Bohlin, Guinier and others are applied.

The schematic view of FIG. 1 shows the Bragg - Brentano modification. A divergent X-ray beam 12 issues either from an X-ray tube ine focus 10 or, less commonly, from the focal line 16 of a (primary) monochromator 14. A specimen 22, usually in the shape of a slab of compressed powder material, is arranged at the center of the so-called goniometer circle 24 so as to be rotatable around an axis that is parallel to the focal line 16 and perpendicular to the circle plane. While the specimen 22 is rotated at a constant angle speed $\theta$, a unit comprising a slit 26 and a detector 28 is swivelled at exactly double speed ($2 \cdot \theta$). As the specimen slab 22 is always at a symmetric position relative to the incident and reflected beams, it produces a para-focussing effect which, however, will weaken with increasing angles of $\theta$ in a wide primary beam. This is due to the fact that the focussing circles, which intersect the focal lines as well as the center of the goniometer circle 24, shrink in size so that conformity of focussing arc and tangent plane (=specimen 22) becomes coarser and finally ceases altogether. Owing to the divergent X-ray beam, the diffractometer circles can be zeroed in only by complex adjustments involving tedious effort. Another drawback is that the para-focussing effect necessitates comparatively large slabs 22 wherein preferred orientations of particles are almost inevitable and, moreover, quite difficult to ascertain exactly.

The Seemann - Bohlin principle is elucidated with the aid of FIGS. 2a and 2b wherein a divergent X-ray beam 12 is seen to be focussed by a monochromator 14 onto a specimen 22 that may be curved or flat. The specimen or sample 22 is arranged at the periphery of the goniometer circle 24, either in a reflection set-up (FIG. 2a) or in a transmission set-up (FIG. 2b); altering the measuring mode thus requires the specimen and the reflex focussing circle to be rearranged, and the reflex profiles differ sharply according to the angular range picked up. For this reason and owing to the inconstancy of the spacing between specimen 22 and detector 28—which latter, therefore, must be moved along the focussing circle by rather intricate kinematic means—this method is more appropriate for film cameras than for automatic diffractometers that are actually intended for measuring the reflexes in a non-stop fashion under conditions as nearly identical as ever possible.

In the arrangements shown in FIGS. 2a and 2b, a primary monochromator 14 will normally be indispensable. By contrast, the set-up of FIG. 1 generally lacks, for reasons of intensity, a primary monochromator but preferably includes a secondary one between detector 28 and specimen 22 in order to eliminate the latter's undesirable radiation such as fluorescent, Compton or radioactive rays the entrance of which into the counter tube commonly used as the detector 28 must be prevented.

By DE-AS No. 1 245 164, a diffraction goniometer has been proposed which aims at using both modes of focussing (FIGS. 2a, 2b) in a single instrument. It provides an auxiliary arm that is rotatable around an axis situated on the goniometer circle and that comprises engaging means for the detector. By arranging the detector such that it is both radially displaceable and coupled to the auxiliary arm's motion, the detector will move on the Seemann-Bohlin focussing circle. However, the instrument affords relatively complex mechanical means due to the coupling and uncoupling of rotatory and translatory motions involved; furthermore, there may be adjustment problems.

OBJECTS OF THE INVENTION

It is an object of this invention to improve on focussing diffractometry in a simple and economical way and, at the same time, to increase measuring accuracy and versatility of the methods and apparatuses employed.

It is another object of the invention to do away with the need to rearrange instrument set-ups when switching from the reflection mode to the transmission mode and vice-versa in the course of structure analysis measurements.

The invention also aims at obtaining accurate focussing of the X-ray beam(s) along the entire goniometer circle.

A further object of the invention consists in enlarging the angular range of the reflexes that can be measured in any single diffraction scan, without sacrificing resolution.

Moreover, the invention contemplates improving on the diffraction resolving power, in particular for investigating specimens that are prone to be affected by air or other environmental factors.

It is yet another object of the invention to enable exploitation of the para-focussing effect in the reflection mode of measurements.

SUMMARY OF THE INVENTION

Basically, the objects are attained by providing in an X-ray diffraction method for determining the structure especially of polycrystalline and liquid substances, using an X-ray beam which is focussed by monochromator means onto the periphery of a circle and which is adapted to be diffracted by a sample specimen arranged in the center of the circle so as to be rotatable around an axis perpendicular to the circle plane, and further using detector means arranged at the periphery of the circle for measuring structure-dependent angles and intensities of the diffracted X-rays, the improvement wherein said circle is arranged such that its periphery intersects the center of said monochromator means.

Thus the unique opportunity is offered of combining, with a minimum of effort, the known methods in a single arrangement enabling scans through the entire 2·θ range, with maximum resolution both for the transmission mode and the reflection mode; at the same time, there is no need for cumbersome rearrangement of set-ups which was inevitable with the conventional techniques. The sample specimen to be studied is always in the center of the goniometer circle at the periphery of which the monochromator means and the detector means are located. Also, the specimen is—in contrast to the Bragg-Brentano method, cf, FIG. 1—in the convergent primary beam at any time, which fact leads to advantages and marginal conditions to be set out below. The comprehensive scanning rendered possible by the invention permits accurate comparison of reflex intensities which is very important for quantitative evaluation and determination of preferred orientations in the specimen.

SPECIALIZATIONS OF THE INVENTION

By selecting the spacing between the X-ray source, or its line focus, and the center of the monochromator means to equal the diameter of the goniometer circle, it is possible to arrange for symmetric focussing and, consequently, to employ pyrolytic graphite monochromators which will not lend themselves to asymmetric treatment. On the other hand, the invention also provides for the use of asymmetrically ground silicon monochromators which yield short distances from the X-ray source to the monochromator center, thus offering more space for accessories to be attached to the goniometer. At any rate, the constantly focussed beam permits to rapidly and conveniently determine the zero point of the 2·θ scale that is fully available.

Where specimens of larger surfaces are to be studied by symmetric reflection, despite the para-focussing effect counteracting the monochromator's convergence action, the invention features means for precisely narrowing the focussed X-ray beam, parallel to the goniometer axis, between the monochromator means and the specimen. A special diaphragm which may comprise a twin slit array will, if accurately adjusted to the specimen center, allow of transmission and reflection scans in a trice, without any displacement of the specimen or even of the goniometer itself, as was necessary according to the prior art. It is also of great advantage that one and the same specimen holder can be used for both the transmission and reflection modes. Samples of powder or liquids can be investigated with excellent resolution. No extra set-up is required for small-angle measurements.

By providing, in an embodiment of the invention, a pivot to the goniometer circle at its point of intersection with the monochromator center, it is easily possible to exchange monochromators so that, in particular, silicon monochromators that feature high angular resolution or graphite monochromators which yield high intensity can be used selectively without affecting the basic set-up of the diffractometer.

Futher features of the invention, especially as stated in the claims, contribute to facilitating the actual measurement work and the instrument operation. The adjustments required are relatively simple and can be performed quickly. Specimen holders as designed according to the invention are adapted to readily receive the various sample shapes and to be rapidly exchanged, in preadjusted positions; specimen slabs may be rotated in their planes during measurements so that preferred orientations may be detected and evaluated or their absence may be established definitely.

IN THE ANNEXED DRAWINGS

FIG. 6 shows a side elevation, partly in cross section, of another specimen holder;

FIG. 7 is a front elevation the specimen holder of FIG. 6;

FIG. 8 shows an exploded sectional view of a base and ring arrangement;

FIG. 9 shows an exploded sectional view of another base and ring arrangement; and FIG. 10 is a front view of the base shown in FIG. 9, with the ring being detached.

DESCRIPTION

Figure 3:
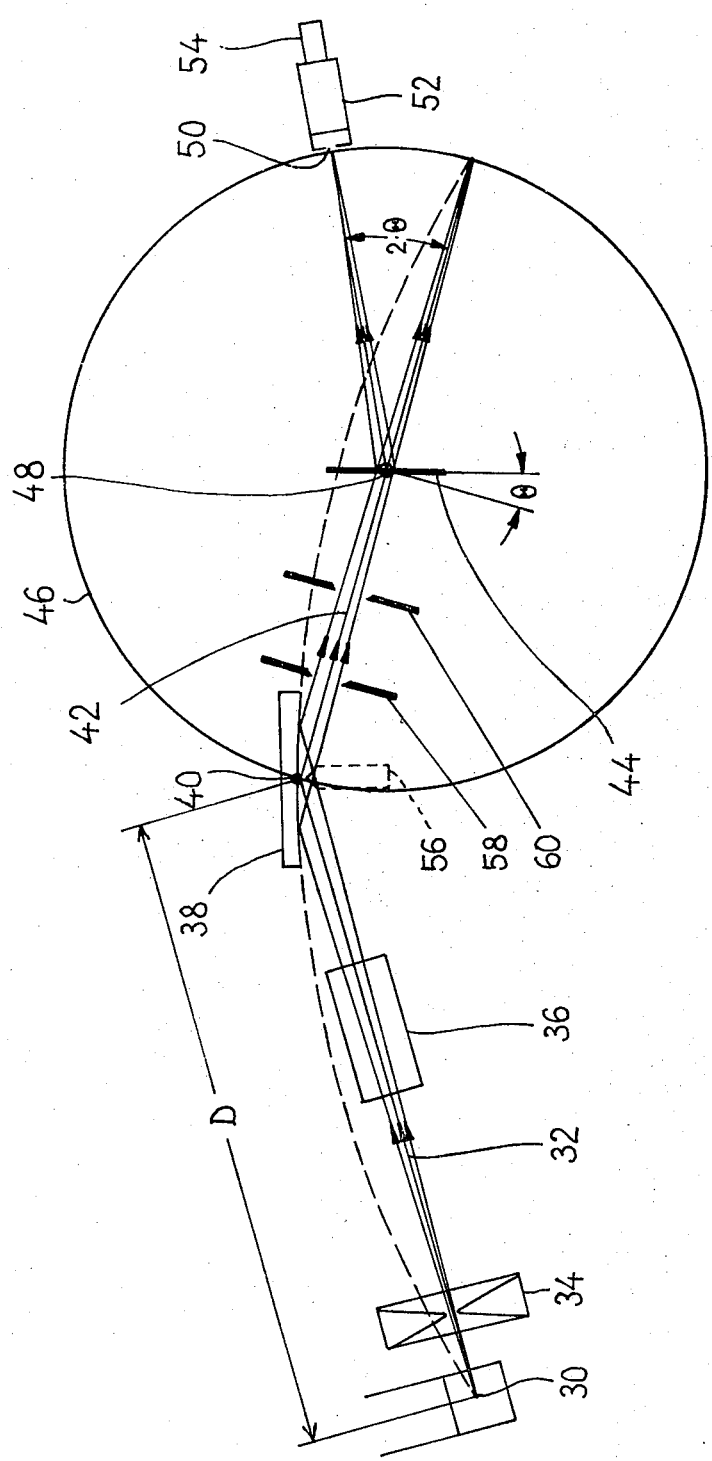
FIG. 3 is a simplified top view of a diffractometer set-up according to the invention.

In the arrangement of FIG. 3, an X-ray tube—preferably of the horizontal type—is used to generate by a line focus 30 a divergent X-ray beam 32 laterally limited from a diaphragm 34. A soller slit unit 36 limits the beam in vertical directions. The beam 32 thus defined impinges on a curved monochromator 38, e.g. made of graphite or silicon, which focusses a monochromatic convergent beam 42 onto the periphery of a goniometer circle 46. In the latter's center there is, parallel to the goniometer axis 48, the sample or specimen 44; in FIG. 3, it is shown to be plate-shaped. Inasmuch as it will not disturb the focussing condition, the present diffractometer's favorable properties can be exploited through the entire 2·θ range.

The distance D between line focus 30 and monochromator 38 on the one hand and between the latter a detector 52 with slit 50 arranged at the periphery of goniometer circle 46 on the other hand may be selected to be, say, 10″ (or roughly 260 mm). This fairly large dimension provides for excellent angular resolution with sufficient intensity and for enough space on the goniometer tray to accomodate accessories, if such are desired. The goniometer ensemble is adapted to be pivoted around an axis 40 that is located in the longitudinal center of monochromator 38. This feature permits easy exchange of monochromators without detracting from the convenient adjustment of the means defining the convergent beam 42 or of the slit and detector set-ups.

In the diffractometer of the type described, the focussing conditions are satisfied if either narrow Debye-Scherrer capillaries or specimen tubes 78 (FIG. 5) or thin specimen disks or slabs (44 in FIGS. 3 and 4; 84 in FIGS. 6 and 8) or foils (not shown) that are coated with powder on either face are adjusted so as to be aligned with the goniometer axis 48. Under these circumstances, the angular resolution will not depend on the width of convergent beam 42 which, therefore, may have a large cross section for whatever sort of transmission scans.

Adequate focussing is, however, also obtained where monochromators designed for a certain radiation such as Cu—K$_\alpha$ will be used with another radiation of slightly different wavelength, e.g. with Cu—K$_\beta$, or if a secondary monochromator (70 in FIG. 4) is inserted between sample 44 and detector 52.

Figure 4:
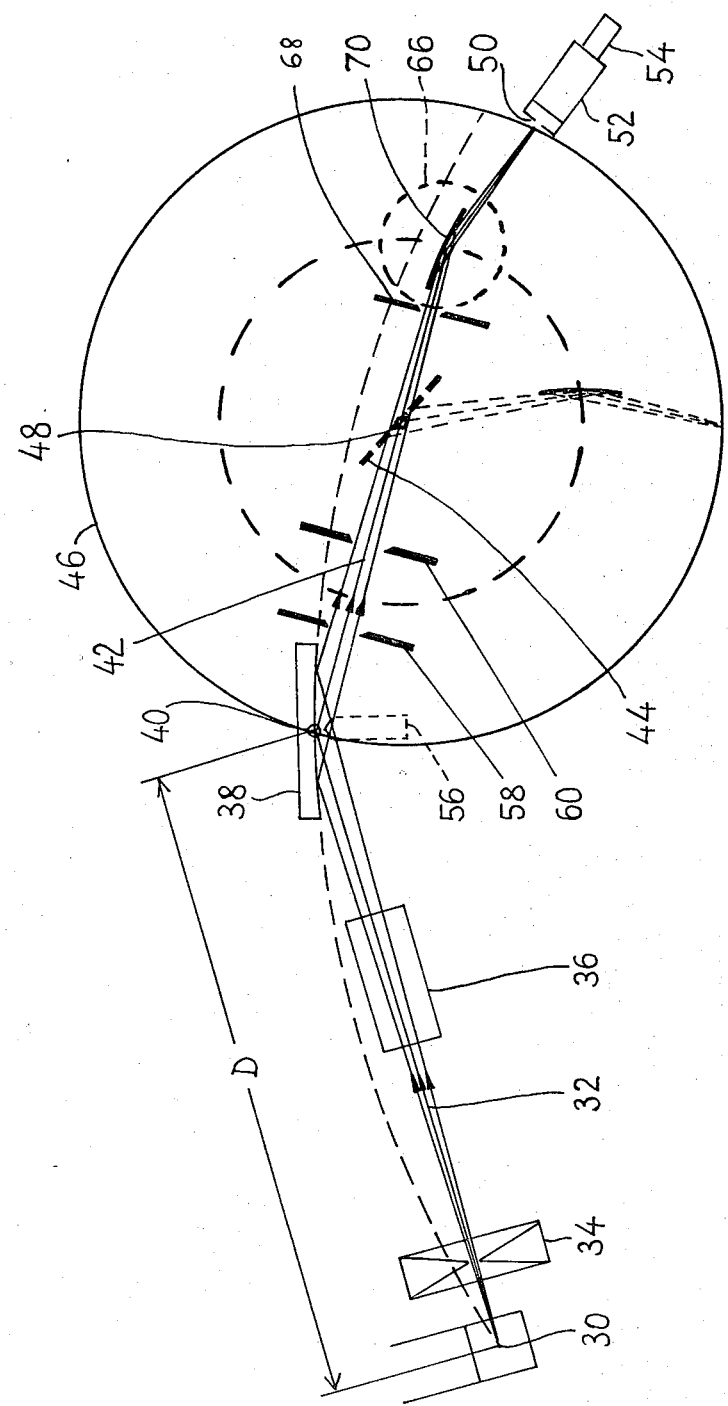
FIG. 4 is a top view similar to FIG. 3 but including a secondary monochromator.
Figure 5:
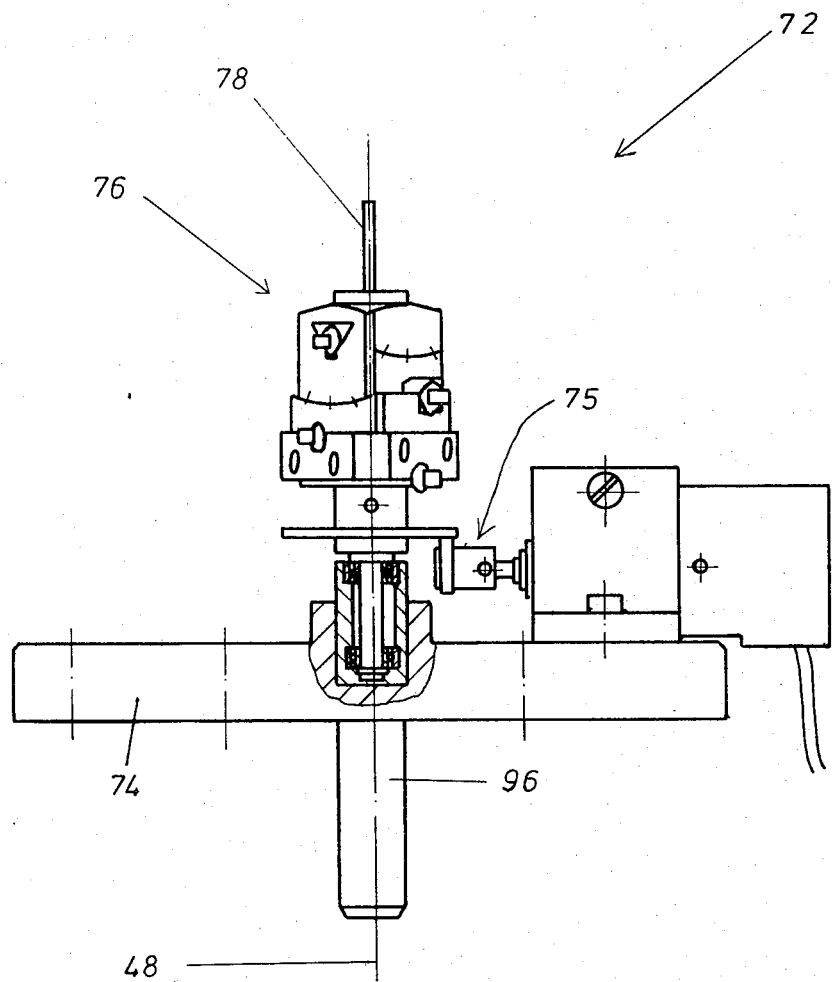
FIG. 5 shows a side elevation, partly in cross section, of a specimen holder.

But where the reflection mode is used to study specimens of larger surfaces, such as thin foils or compacted slabs, these may seriously disturb the focussing conditions. Such trouble is removed despite the sample being in the goniometer center if an array of diaphragms and slits is provided as shown in FIGS. 3 and 4 where edge 56 opposite the center of monochromator 38 forms a diaphragm (indicated by phantom lines) that is supplemented by a precision diaphragm 58 and a scatter slot 60. This array serves to reduce the width of convergent beam 42 to a narrow line accurately parallel to goniometer axis 48. A maximum line width of, say, 0.2 mm (7.9 mil) may be adjusted so as to warrant both high angular resolution for reflection scans and sufficient intensity for transmission scans.

In order to achieve a sufficiently narrow beam 42, the diaphragm and slit array according to the invention is equipped with precision adjustment means such as micrometer screws. Edge 56 may be guided for parallel displacement in its plane relative to the longitudinal center of monochromator 38. The following diaphragm 58 may comprise movable wall sections of a cylindrical casing (not shown) that encompasses monochromator 38. A twin slit array will generally be required in the small-angle range, i.e. with $\theta$ equalling 0.5 to 2 degrees. When working in the reflection mode or for combined reflection-transmission scans, a precision diaphragm should be placed as close to the sample or specimen 44 as ever possible.

The goniometer circle 46 is scanned by the detector unit that is movable along its periphery and that may comprise slit 50, a counter tube 52 and a counter tube arm 54. The invention contemplates also to encompass large portions of the 2·$\theta$ range or all of it by a locally sensitive detector, in particular by a curved wire chamber of the type disclosed by V. Perez-Mendez et al. in Nuclear Instruments and Methods vol. 156 (1978), pp. 53 to 56.

FIG. 4 shows an embodiment including a swivel mount 66 (indicated by broken lines) which can be moved along an inner circle (also shown by broken lines) concentric to goniometer circle 46. Swivel mount 66 support a slit 68 as well as a secondary monochromator 70 in order to remove undesirable radiation issuing from sample 44. For correct X-ray optics, arm 54 and swivel mount 66 may comprise suitable guide means such as dovetail mechanisms and adjusting screws as well as locking means (not shown).

FIGS. 5 to 10 show various means for holding the samples or specimens for use in the diffractometer according to FIGS. 3 or 4. Sample holders 72 (FIG. 5) and 79 (FIGS. 6 and 7) are preferred for quick exchange and adjustment of samples 44 that may be rod-shaped, as in the example of FIG. 5, or may be plane by way of foils or slabs of moderate wall thickness which are suited for both back-reflection and transmission scans, whereas thick slabs will lend themselves to back-reflection diagrams only.

Sample holder 72 (FIG. 5) includes a support disk 74 having a wheel and disk drive 75 for a rotatable goniometer head 76 onto which Debye-Scherrer capillaries or specimen tubes 78 may be fixed in customary manner, e.g. by means of stick-on wax, sealing wax, piceine, Canada balsam, etc. Specimen tube 78 may be optically aligned by using the cross wires of a microscope (not shown) and adjusting the goniometer head 76 in all its degrees of freedom; for aligning the axis of specimen tube 78 with the goniometer axis 48, base disk 74 may comprise a setting device such as a conventional compound slide (not shown). A plug-in shaft 96 of base disk 74 can be fitted into a corresponding seat (not shown) of the goniometer tray.

Selectively, the same seat of goniometer tray (46) may receive an identical plug-in shaft 96 of sample holder 79 (FIGS. 6 and 7) that may be likewise preadjusted. As will be seen from FIG. 6, base disk 92 of this embodiment is stepped in the fashion of a half-cylinder to provide a vertical step face 94 to which a plane plate 80 may be secured verticaly. A round recess 82 in plate 80 (see also FIG. 7) serves to seat a round base 85 for a specimen disk 84 which is inserted into base 85 in axial direction unto a stop 87 and locked in this position by means of a socket ring 86 (shown in FIG. 8, too). The periphery of base 85 forms a friction rim 88 gripped by rollers 89, 91 which are rotatably supported by plate 80. In the embodiment shown, two rollers 89 may idle while a third roller 91 serves as a friction drive powered by motor 90 for rotating the unit of base 85 and sample 84 in the plane of plate 80.

Whilst sample 84 may be a compacted powder slab which, if rather thick, permits X-ray diffraction only in the back-reflection mode, foils and thin slabs 100 that are also suitable for transmission scans may be supported by a similar base 101 (FIGS. 9 and 10) to be selectively seated in sample holder 79. Once foil or slab 100 has been placed on a holding ring 103, magnets 102 (e.g. in the shape of strips or ledges seen in FIG. 10) may act to pull ring 103 to a stop 104 in base 101, which latter also comprises a friction rim 88 to be gripped and driven by rollers 89, 91 of sample holder 79.

It will now be evident that these devices allow accurate adjustment of whatever sample sort in the center of the goniometer. Thus the 2·$\theta$ range can be fully utilized with all the exactitude warranted by focussing according to the invention. Zeroing-in is performed by 2·$\theta$ steps of 0.005 degrees (=0.3 arc minutes) or less, as the mechanical accuracy of the gear drive used (not shown) may be even better. Two step motors may be provided for effecting angular increments of 0.0025 degrees (=0.15 angular minutes) indicated by an electronic angle display (not shown). A miniature computer (likewise not shown) may be provided for motion control, e.g. a twin-diskette system of the type 28KW LSI-11 supplied by Digital Equipment Corporation.

Even in routine work, angular resolutions of 0.135 degrees (=8.1 arc minutes) by use of a graphite monochromator and 0.09 degrees with a silicon monochromator, respectively, can be attained normally, these data to indicate the full width at half-maximum (FWHM) of the $SiO_2$ triplet 122/203/301 with Cu—K$_\alpha$ radiation. It depends on the particular type of measurement undertaken whether maximum angular resolution or maximum intensity are to be aimed at; using graphite monochromators, the integrated intensities available are about five times as large as by the use of silicon monochromators.

Comparing FWHM values of Debye-Scherrer reflexes with those of back-reflection diagrams, differences of up to 0.04 degrees (=2.4 arc minutes) in favor of the reflection scans are found. By means of modified Lorentz functions, the reflex profiles can be established for all types of diagrams or scans to satisfactory approximation.

Figure 2A:
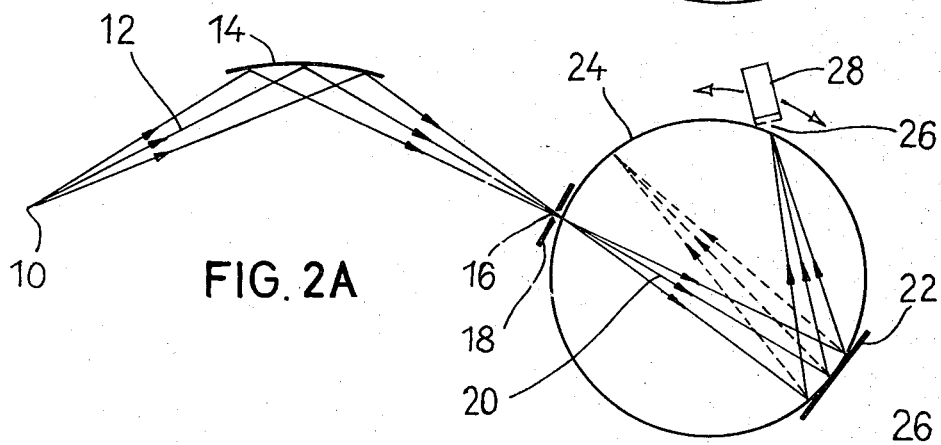
Figure 2B:
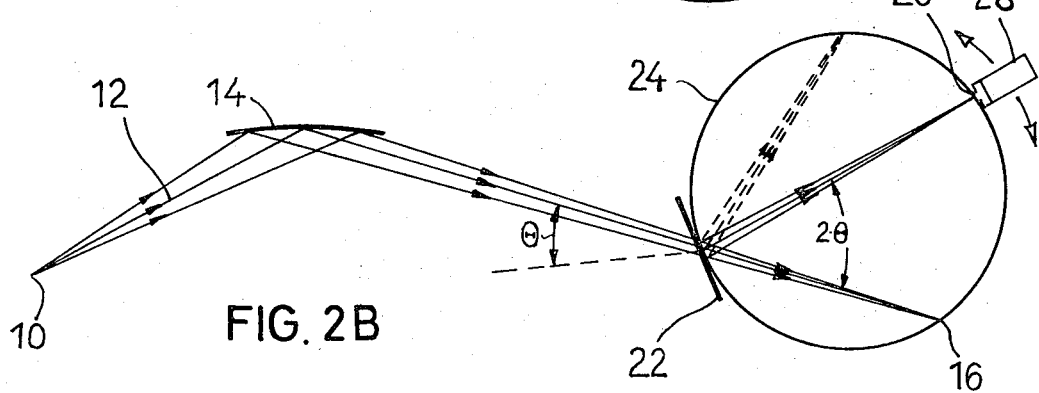

It will be realized that by the invention, convergent focussing of a monochromatic primary beam 42 is directed onto the sample 44 as is also the case with the Seemann-Bohlin method (FIG. 2b). But unlike the latter, the invention provides for locating both the curved monochromator 38 and the detector array 50, 52, 54 on the periphery of goniometer circle 46.

Figure 1:
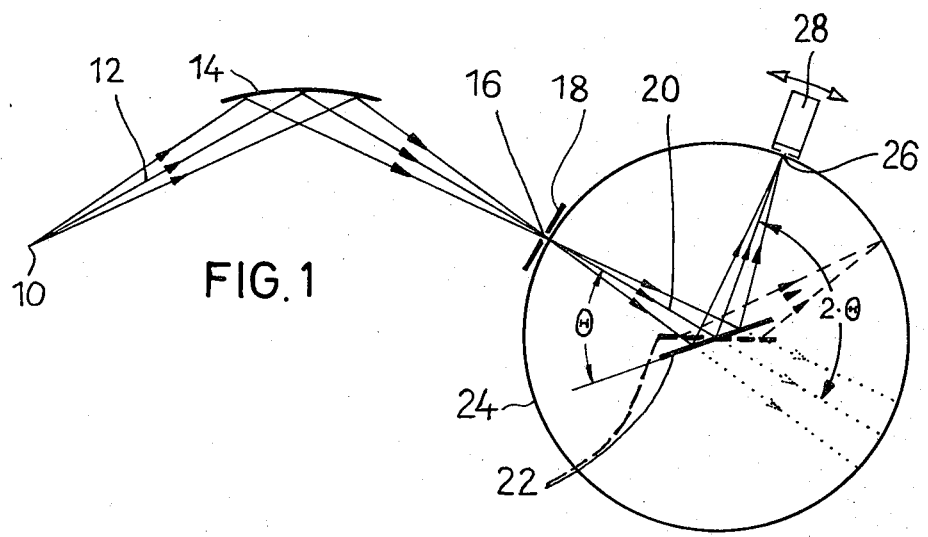
FIGS. 1, 2a and 2b represent the prior art as discussed above.

In addition, it will be seen that by the invention, the sample 44 is in the center of goniometer circle 46 as according to the Bragg-Brentano method (FIG. 1), and the focussing circle radii also decrease with growing Bragg angles $\theta$. But in contrast to this prior art, the sample 44 is irradiated by the convergent beam 42 which is accurately focussed on goniometer circle 46 along which the detector array 50, 52, 54 is moved, and the diaphragm and slit array 56, 58, 60 provides the additional possibility of defining a narrowed beam 42 permitting symmetric reflection scans even with specimens of larger surfaces despite their para-focussing countereffect.

Apart from the adjustments necessary, a full measuring program includes the following procedures: testing operation readiness for the various diffracting modes; quick peak search; automatic data measurement with real time diagrams; error compensation and profile fit; indexing unknown powder diagrams and associating the measured data to stored data of known structures; computing the theoretical powder diagrams and refining the analysis by powder data. It is to be emphasized that combined scans in the reflection and transmission modes allow of accurate intensity comparison, enabling detection of even small fractions of preferred orientation in the polycrystalline or liquid samples studied; moreover, quantitative evaluation of intensity differences between transmission and reflection scans—which appear to be averaged in the Debye-Scherrer diagrams—serves to establish and verify exact structures.

While preferred embodiments have been illustrated and explained hereinabove, it should be understood that numerous variations and modifications will be apparent to one skilled in the art without departing from the principles of the invention which, therefore, is not to be construed as being limited to the specific forms described.

We claim:

1. In an X-ray diffraction method for determining the structure of a polycrystalline or liquid substance, which method includes
   focusing an X-ray beam by curved monochromator means onto the periphery of a circle,
   arranging a specimen sample of the substance in the center of the circle so that it is rotatable around an axis that is perpendicular to the plane of the circle, and
   measuring the structure dependent angles and intensities of the X-rays diffracted by the specimen sample by a detector means located at the periphery of the circle,
the improvement comprising arranging said circle so that its periphery intersects the center of said monochromator means.

2. A method according to claim 1 which additionally includes positioning the source of said X-ray beam away from the center of said monochromator at a distance which is equal to the diameter of said circle.

3. A method according to any one of claims 1 or 2, wherein said focused X-ray beam is, between said monochromator means and said sample specimen, narrowed such that the main direction of the beam's cross section is parallel to said circle axis.

4. A method according to any one of claims 1 or 2, wherein said circle is adapted to be pivotable in its plane around an axis (a) that is perpendicular thereto and (b) that extends through said circle where the circle intersects said center of said monochromator means.

5. In an X-ray diffractomer for determining the structure of a polycrystalline or liquid substance which includes
   an X-ray tube for generating an X-ray beam,
   a goniometer circle,
   a curved monochromator means for focusing an X-ray beam issuing from the line focus of said X-ray tube onto the periphery of said goniometer circle,
   a specimen holder for said substance mounted in a plane at the center of said circle, said specimen holder being adapted to be rotated around an axis that is perpendicular to the holder plane, and
   detector means arranged at the periphery of said circle which is adapted to measure the structure dependent angles and intensities of the diffracted X-rays,
the improvement comprising that said goniometer circle being arranged so that it intersects the longitudinal center of said monochromator means.

6. A diffractometer according to claim 5 wherein the distance between said longitudinal center of said monochromator means and said X-ray tube line focus being equal to the diameter of said goniometer circle.

7. A diffractometer according to any one of claims 5 or 6 wherein said goniometer circle is pivotable at the point where its periphery intersects said longitudinal center of said monochromator means, around an axis parallel to said line focus and to said goniometer axis.

8. A diffractometer according to any one of claims 5 or 6 wherein said specimen holder includes a support disk for a goniometer head designed to receive a specimen tube and adapted to adjust the latter so as to be aligned with said goniometer axis.

9. A diffractometer according to claim 8 wherein said support disk is adapted to be mounted to said goniometer circle.

10. A diffractometer according to any one of claims 5 or 6 comprising drive means for said goniometer circle such that its angular speed is exactly half of the speed of said detector means along the periphery of said goniometer circle, wherein said drive means is electronically coupled to said detector means in a rigid relationship.

11. A diffractometer according to any one of claims 5 or 6 wherein said detector means includes a Perez-Mendez curved wire chamber.

12. A diffractometer according to any one of claims 5 or 6 wherein a secondary monochromator means is arranged in front of said detector means, said secondary monochromator means including a support for attachment to a counter tube arm.

13. A diffractometer according to any one of claims 5 or 6 wherein said specimen holder includes a plate having a round recess for positively receiving a base means for a specimen adapted to be aligned with said goniometer axis.

14. A diffractometer according to claim 13 wherein said base means periphery is frictionally held by three rollers.

15. A diffractometer according to claim 13 wherein said base means is arranged to be rotatable in its plane.

16. A diffractometer according to claim 15 wherein a driving friction roller is engaged to the rim of said base means.

17. A diffractometer according to claim 13 wherein said plate is adapted to be attached to a vertical step face of a diagonally stepped disk and to be adjusted relative to said goniometer axis.

18. A diffractometer according to claim 17 wherein said stepped disk is adapted to be mounted to said goniometer circle.

19. A diffractometer according to any one of claims 5 or 6 wherein there is at least one diaphragm means between said monochromator means and said sample specimen for precisely narrowing said focused X-ray beam parallel to said goniometer axis.

20. A diffractometer according to claim 19 wherein said diaphragm means is arranged immediately in front of said sample specimen for narrowing said focussed X-ray beam with reflection measurements or with combined reflection-transmission scans.

21. A diffractometer according to claim 19 wherein said diaphragm means is arranged opposite said longitudinal center of said monochromator means.

22. A diffractometer according to claim 19 wherein said diaphragm means is arranged immediately behind said monochromator means and is attached to its support.

23. A diffractometer according to claim 19 wherein one of said diaphragm means comprises shiftable wall sections of a cylindrical casing of said monochromator means.

24. A diffractometer according to claim 19 wherein said diaphragm means comprises a twin slit array consisting of a precision diaphragm and a scatter slit.

* * * * *